US011547754B2

(12) United States Patent
Song

(10) Patent No.: US 11,547,754 B2
(45) Date of Patent: Jan. 10, 2023

(54) H5 AVIAN INFLUENZA VACCINE STRAIN WHICH DIFFERENTIATES INFECTED FROM VACCINATED ANIMALS, PREPARATION METHOD THEREFOR, AND APPLICATION

(71) Applicant: Jiasheng Song, Zhejiang (CN)

(72) Inventor: Jiasheng Song, Zhejiang (CN)

(73) Assignee: Zhejiang Difference Biological Technology Co., LTD., Zhejiang (CN)

( * ) Notice: Subject to any disclaimer, the term of this patent is extended or adjusted under 35 U.S.C. 154(b) by 62 days.

(21) Appl. No.: 16/765,770

(22) PCT Filed: Jun. 1, 2018

(86) PCT No.: PCT/CN2018/089519
§ 371 (c)(1),
(2) Date: May 20, 2020

(87) PCT Pub. No.: WO2019/100686
PCT Pub. Date: May 31, 2019

(65) Prior Publication Data
US 2020/0282044 A1    Sep. 10, 2020

(30) Foreign Application Priority Data

Nov. 21, 2017 (CN) .......................... 201711167959.4

(51) Int. Cl.
*A61K 39/12*       (2006.01)
*C12N 15/113*      (2010.01)
*C12N 7/00*        (2006.01)
*A61K 39/00*       (2006.01)

(52) U.S. Cl.
CPC ............... *A61K 39/12* (2013.01); *C12N 7/00* (2013.01); *C12N 15/113* (2013.01); *A61K 2039/5252* (2013.01); *A61K 2039/53* (2013.01); *A61K 2039/552* (2013.01); *C12N 2760/16122* (2013.01); *C12N 2760/16221* (2013.01); *C12N 2760/16234* (2013.01)

(58) Field of Classification Search
None
See application file for complete search history.

(56) References Cited

U.S. PATENT DOCUMENTS

2008/0118531 A1* 5/2008 Hoffmann ............. A61K 39/12
                                                    424/209.1
2020/0282044 A1* 9/2020 Song ..................... C07K 14/005

FOREIGN PATENT DOCUMENTS

CN       1970081 A     5/2007
CN     107281478 A    10/2017

OTHER PUBLICATIONS

Baker et al. (Journal of Virology. 2014; 88 (18): 10778-10791).*
Sequence alignment of Seq ID 5 with Geneseq db access No. ALS14245 in USPgPub 20070231348 entered Dec. 2007.*
Flandorfer et al. (Journal of Virology. 2003; 77 (17): 9116-9123).*
Ping et al. (PNAS. 2016; 113 (51): E8296-E8305).*
Sequence alignment of instant Seq ID No. 9 with Geneseq db access No. ATT37499 in WO2008138120 Yao et al. entered Jan. 2009.*
Air, "Sequence Relationships Among the Hemagglutinin Genes of 12 Subtypes of Influenza A Virus", Proc. Natl. Acad. Sci. USA, vol. 78, No. Dec. 12, 1981, pp. 7639-7643.
Liu et al., Progress of Reverse Genetics Technique in Influenza Virus, Progress in Biochemistry and Biophysics, vol. 35, No. 8, 2008, pp. 867-874. (English abstract).
Mitnaul et al., "Balanced Hemagglutinin and Neuraminidase Activities Are Critical for Efficient Replication of Influenza A Virus", Journal of Virology, vol. 74, No. 13, Jul. 2000, pp. 6015-6020.
Murakami et al., "Growth Determinants for H5N1 Influenza Vaccine Seed Viruses in MDCK Cells", Journal of Virology, vol. 82, No. 21, Nov. 2008, pp. 10502-10509.
Nobusawa et al., "Comparison of Complete Amino Acid Sequences and Receptor-Binding Properties among 13 Serotypes of Hemagglutinins of Influenza A Viruses", Virology, vol. 182, 1991, pp. 475-485.
Rudneva et al., "Influenza A Virus Reassortants with Surface Glycoprotein Genes of the Avian Parent Viruses: Effects of HA and NA Gene combinations on Virus Aggregation", Archives of Virology, vol. 133, 1993, pp. 437-450.
Wagner et al., "Functional Balance Between Haemagglutinin and Neuraminidase in Influenza Virus Infections", Reviews in Medical Virology, vol. 12, 2002, pp. 159-166.
Li et al., "Roles of Different Domains of Influenza Virus Neuraminidase", Life Science Research, vol. 9, No. 2 (Suppl.), Jul. 2005, pp. 55-61. (English abstact).
International Search Report for PCT/CN2018/089519 dated Sep. 6, 2018. (English Translation).
Gaymard et al., Functional balance between Neuraminidase and Hemagglutinin in influenza viruses, Clinical Microbiology and Infection, Jul. 3, 2016, pp. 1-27.
Hiti et al., Complete Nucleotide Sequence of the Neuraminidase Gene of Human Influenza Virus AWSN33, Journal of Virology. Feb. 1982, pp. 730-734.
Kosik et al., Influenza Hemagglutinin and Neuraminidase Yin-Yang Proteins Coevolving to Thwart Immunity, www.mdpi.com/journal/viruses, Viruses 2019, 11, 346 pp. 1-18.
Wantanabe et al., The Changing Nature of avian influenza A virus (H5N1), Trends In Microbiology, Jan. 2012, vol. 20, No. 1, pp. 1-20.
Yang et al., Variation in Influenza B Virus Epidemiology by Lineage, China, Emerging Infectious Diseases, www.cdc.gov/eld, vol. 24, No. 8, Aug. 2018, pp. 1536-1540.

* cited by examiner

*Primary Examiner* — Shanon A. Foley
(74) *Attorney, Agent, or Firm* — Foley & Lardner LLP

(57) ABSTRACT

Provided are an H5 avian influenza vaccine strain which differentiates infected from vaccinated animals, a preparation method therefor, and an application. The vaccine strain uses an NA protein of influenza B as a label, and has application value and public health significance for the prevention, control and decontamination of H5 avian influenza.

16 Claims, 1 Drawing Sheet
Specification includes a Sequence Listing.

A/B chimeric NA gene

```
5'  ATG            cDNA              TAA      3'
   NCR  CT  TM   Influenza B virus NA      NCR
   5'-end packaging                  3'-end packaging
   signal sequence                   signal sequence
```

NCR: Noncoding region, CT: Intracellular region (6~7aa),
TM: Transmembrane region (24~32aa)

H5 AVIAN INFLUENZA VACCINE STRAIN WHICH DIFFERENTIATES INFECTED FROM VACCINATED ANIMALS, PREPARATION METHOD THEREFOR, AND APPLICATION

CROSS-REFERENCE TO RELATED APPLICATIONS

This application is a national stage application under 35 U.S.C. § 371 of PCT Application No. PCT/CN2018/089519, filed Jun. 1, 2018, which claims priority to Chinese application no. CN201711167959.4, filed Nov. 21, 2017, each of which is incorporated herein by reference in its entirety.

SEQUENCE LISTING

The instant application contains a Sequence Listing which has been filed electronically in ASCII format and is hereby incorporated by reference in its entirety. Said ASCII copy, created on Jul. 30, 2021, is named 125819-0102 SL ST25.txt and is 13,851 bytes in size.

TECHNICAL FIELD

The disclosure belongs to the field of genetic engineering vaccines, relates to a preparation method of an H5 avian influenza vaccine strain which differentiates infection from vaccination, and an application thereof.

BACKGROUND

Avian influenza virus belongs to the genus of influenza virus, the family of Orthomyxoviridae. Influenza viruses are classified into types A, B, and C in terms of antigenic diversity, wherein influenza A viruses have a broad species tropism (including avian, human, swine, etc.), with a strong pathogenicity and huge damages. Influenza B viruses are primarily limited to the human population, although rare infections of seals have been documented, with a relatively low pathogenicity. Influenza C viruses are only found in human and swine. The genomes of influenza A and B can be divided into 8 gene segments in total: PB2, PB1, PA, NP, HA, NA, M, and NS. Once being infected, hosts may generate a large amount of antibodies to HA, NA, M1 and NP proteins, wherein HA may induce major neutralizing antibodies directly. It is found in previous researches that the four major antibodies against HA, NA, M1 and NP induced by viruses of types A and B have no serological cross-reactivity. The antigenic diversity of the HA and NA proteins of the influenza virus is used to classify influenza viruses into different subtypes (HnNn), wherein there are 18 subtypes for HA and 11 subtypes for NA, which may produce 198 (18×11) subtypes theoretically, however, there are only a few advantage subtypes in nature actually (e.g., H5N1, H7N9, H9N2, etc.). The sequence homologies among different subtypes of HA proteins are between 40%-80% (Air G M. Proceedings of the National Academy of Sciences of the United States of America, 1981, 78(12):7639. Nobusawa E, et al. Virology, 1991, 182(2):475-485). There are no subtypes for influenza B, with high similarities between each virus strain gene. According to the antigenic variant, influenza B viruses are currently divided into only two lineages, Victoria group (named following B/Victoria/2/1987) and Yamagata group (named following B/Yamagata/16/1988) respectively. There are almost all subtypes of influenza A in avian species, playing important roles in the storage and evolution of the virus. The global epidemic of avian influenza has caused huge economic losses to the poultry industry, the cases of human infections with avian influenza are increasing gradually with the gradual adaptation of avian influenza viruses to human. Compared with seasonal human influenza, human infections with avian influenza are characterized by severe morbidity and high mortality, greatly threatening the public health safety. In numerous subtypes of avian influenza, H5 is extremely hazardous, causing huge economic losses. Highly pathogenic H5 avian influenza may result in 100% death of the poultry in a few days, and may infect human directly. Infections in human are serious in symptoms and high in mortalities. The thoroughly decontamination of avian influenza in the farms is the most effective means for eliminating the risks to the food safety and the public health.

At present, vaccination is one of the most effective methods for preventing and controlling avian influenza. The vaccine strains constructed with the internal gene of the chick-embryo highly adaptable strain PR8 as the background with the external genes (HA, NA) which are substituted for the epidemic strains are safe, effective and inexpensive, being applied most extensively in China, and playing important roles in preventing and controlling of avian influenza. However, this kind of whole virus inactivated vaccine cannot serologically differentiate infected from vaccinated animals, causing a great obstacle in the monitoring and decontamination of avian influenza virus. In the life cycle of virus, the HA protein attaches the virus to the cell surface by binding to sialic-acid-containing receptors and promotes viral penetration by mediating fusion of the endosomal and viral membranes, and the NA protein functions as a homotetramer, facilitating the mobility of virions by removing sialic acid residues from viral glycoproteins and infected cells during both entry and release from cells. Therefore, a balance of competent HA and NA (the matching of HA-NA) activities appears critical and may directly affect the replication capacities and growth properties of influenza viruses (Mitnaul L J, Matrosovich M N, Castrucci M R, et al. Balanced Hemagglutinin and Neuraminidase Activities Are Critical for Efficient Replication of Influenza A Virus[J]. Journal of Virology, 2000, 74(13):6015-20.). Therefore, selection of viruses with HA and NA functional balance is one of the keys to develop excellent vaccine strains (Murakami S, et al. Growth Determinants for H5N1 Influenza Vaccine Seed Viruses in MDCK Cells[J]. Journal of Virology, 2008, 82(21):10502.). For ensuring the functional balance between vaccine strains HA and NA, the two genes are generally derived from the same virus strain. Introduction of heterogenous NAs may disrupt the functional balance between HA-NA, thus reducing the growth and replication capacities of viruses, even resulting in recombinant viruses unable to be rescued. In general, such risks would increase continually as the similarity of the introduced NA gene is reduced (compared with homogenous NAs). Replacements among different subtypes of NA always affect biological properties in terms of replication and growth, of the rescued recombinant viruses. This is also the reason why there are only few advantageous subtype combinations in nature (e.g., common H9N2, H5N1, H7N9, etc.), rather than random combinations of HA-NA (e.g., rare H9N1, H5N9, etc.)(Wagner R et al, Functional balance between haemagglutinin and neuraminidase in influenza virus infections[J]. Reviews in Medical Virology, 2002, 12(3):159). Rudneva et al used different combinations of N1 gene and subtypes of HA gene to generate recombinant viruses, and found that the growth properties of the recombinant viruses of the rescued H3, H4, H10 and H13 on chick-embryos are poorer than their wild-type viruses (Rudneva I A et al. Influenza A virus reassortants with surface glycoprotein genes of the avian parent viruses: effects of HA and NA gene combinations on virus aggregation. [J]. Archives of Virology, 1993, 133(3-4):437-450). Due to the great difference of NA protein in types B and A influenza viruses (with the similarity <30%), the success probability of obtaining the A/B chimeric virus by introducing type B NA is small. Moreover, there may be defects in the growth properties of the rescued A/B NA chimeric viruses, and it may needed to be adapted by serial passages in vitro. However, serial passages may introduce adaptive mutations, causing the risk of antigenic drift, thus resulting in great differences between the antigenicity of the prepared vaccine strains and the original wild-type epidemic strains.

Although the existing H5 whole virus inactivated vaccines do have advantages such as being reliable in terms of immune effect and low cost, the fact that they cannot serologically differentiate infected from vaccinated animals (DIVA) seriously affects monitoring on the virus epidemic, thus hindering the thoroughly decontamination of H5 avian influenza in the farms. The presence of highly pathogenic avian influenza diseases in the farms cannot be eliminated completely, such that the highly pathogenic H5 virus has the risk of persistently threatening the public health. Therefore, it is needed currently to prepare a new H5 avian influenza vaccine strain which can differentiate infection from vaccination.

SUMMARY

To resolve the above issues, the application develops a preparation method of a new H5 avian influenza vaccine strain which differentiates infection from vaccination by introducing the NA gene of influenza B as a label. There is no need for the vaccine strains prepared with chimeric NA gene to be adapted by serial passages in vitro, thus avoiding the risk of antigenic variation caused by serial passages. Moreover, in the present invention, through partial deletion of NS1 proteins and weakening modification of HAs, the safety property of the rescued vaccine strains is obviously superior to that of the ordinary vaccine strains. Therefore, the present invention provides a preparation method of an H5 avian influenza vaccine which is safe and effective, low in production cost and can serologically differentiate infected from vaccinated animals, which has great application values and prominent public health significance.

The object of the present invention is to provide an H5 avian influenza vaccine strain which differentiates infection from vaccination and an application thereof.

Another object of the present invention is to provide a preparation method of an H5 avian influenza vaccine strain which differentiates infection from vaccination.

The technical solutions employed in the present invention are as below:

An application of a label gene sequence in the preparation of an H5 avian influenza vaccine strain which differentiates influenza A virus infection from vaccination, the label gene sequence containing a DNA sequence for coding an influenza B virus NA protein extracellular region amino acid sequence, or containing a DNA sequence for coding an amino acid sequence having at least 90% homology, or at least 92% homology, or at least 95% homology, or at least 98% homology with the extracellular region amino acid sequence;

alternatively, the label gene sequence containing a DNA sequence for coding the extracellular region amino acid sequence in influenza B virus NA gene, or containing a sequence having at least 90% homology, or at least 92% homology, or at least 95% homology, or at least 98% homology with the DNA sequence;

alternatively, the label gene sequence is a DNA sequence for coding influenza B virus NA protein, or a DNA sequence for coding an amino acid sequence having at least 90% homology, or at least 92% homology, or at least 95% homology, or at least 98% homology with the NA protein amino acid sequence;

alternatively, the label gene sequence is a DNA sequence of influenza B virus NA gene, or a sequence having at least 90% homology, or at least 92% homology, or at least 95% homology, or at least 98% homology with the DNA sequence.

Furthermore, the H5 avian influenza vaccine strain further contains an H5 subtype HA gene or a mutated H5 subtype HA gene; the mutated H5 subtype HA gene is capable of mutating the amino acid sequence RERRRKRGLF (SEQ ID NO: 8) in the wild type HA protein into RETRGLF (SEQ ID NO: 9).

Furthermore, the influenza B virus includes influenza B viruses of Victoria group and Yamagata group.

Furthermore, the influenza B virus specifically includes, but not limited to, virus strains B/Massachusetts/2/2012, B/Brisbane/60/2008, B/Yamagata/16/1988, B/Malaysia/2506/04.

Furthermore, the label gene sequence further contains packaging signal sequences at its both ends, the packaging signal is a packaging signal of H1 subtype NA, or a packaging signal sequence having at least 80% homology, or at least 85% homology, or at least 90% homology, or at least 95% homology with the packaging signal of H1 subtype NA.

Furthermore, the label gene sequence further contains packaging signal sequences at its both ends, wherein the 5'-end packaging signal sequence includes the noncoding region sequence, the intracellular region sequence, and the transmembrane region sequence.

Furthermore, the intracellular region sequence encodes 5-7 amino acids, with the amino acid sequences within the cell.

Furthermore, the transmembrane region sequence encodes 2432 amino acids, with the amino acid sequences in the transmembrane region.

Furthermore, the 5'-end packaging signal sequence of the label gene sequence is SEQ ID NO:3, or a sequence having at least 80% homology, or at least 85% homology, or at least 90% homology, or at least 95% homology with SEQ ID NO:3.

Furthermore, the label gene sequence further contains packaging signal sequences at its both ends, wherein the 3'-end packaging signal sequence is SEQ ID NO:4, or a sequence having at least 80% homology, or at least 85% homology, or at least 90% homology, or at least 95% homology with SEQ ID NO:4.

A preparation method of an H5 avian influenza vaccine strain which differentiates influenza A virus infection from vaccination, including the following steps: the label gene sequence is rescued with an HA gene or a mutated H5 subtype HA gene of H5 avian influenza virus over a reverse genetic system to obtain a recombinant vaccine strain, that is an H5 avian influenza vaccine strain which differentiates influenza A virus infection from vaccination;

the mutated H5 subtype HA gene is capable of mutating the amino acid sequence RERRRKRGLF (SEQ ID NO: 8) in the wild type HA protein into RETRGLF (SEQ ID NO: 9);

the label gene sequence containing a DNA sequence for coding an influenza B virus NA protein extracellular region amino acid sequence, or containing a DNA sequence for coding an amino acid sequence having at least 90% homology, or at least 92% homology, or at least 95% homology, or at least 98% homology with the extracellular region amino acid sequence;

alternatively, the label gene sequence containing a DNA sequence for coding an extracellular region amino acid sequence in influenza B virus NA gene, or containing a sequence having at least 90% homology, or at least 92% homology, or at least 95% homology, or at least 98% homology with the DNA sequence;

alternatively, the label gene sequence is a DNA sequence for coding influenza B virus NA protein, or a DNA sequence for coding an amino acid sequence having at least 90% homology, or at least 92% homology, or at least 95% homology, or at least 98% homology with the NA protein amino acid sequence;

alternatively, the label gene sequence is a DNA sequence of influenza B virus NA gene, or a sequence having at least 90% homology, or at least 92% homology, or at least 95% homology, or at least 98% homology with the DNA sequence.

Furthermore, the label gene sequence further contains packaging signal sequences at its both ends.

Furthermore, the 5'-end packaging signal sequence of the label gene sequence is SEQ ID NO:3, or a sequence having at least 80% homology, or at least 85% homology, or at least 90% homology, or at least 95% homology with SEQ ID NO:3.

Furthermore, the 3'-end packaging signal sequence of the label gene sequence is SEQ ID NO:4, or a sequence having at least 80% homology, or at least 85% homology, or at least 90% homology, or at least 95% homology with SEQ ID NO:4.

Furthermore, there are additional 6 PR8 internal genes used during the rescue with the reverse genetic system which are the wild type NS or a mutated ΔNS gene and PB2, PB1, PA, NP, M; wherein ΔNS is a mutated NS gene, the nucleotide sequence of ΔNS is as shown in SEQ ID NO:5.

An H5 avian influenza vaccine strain which differentiates influenza A virus infection from vaccination, which is named as H5 avian influenza vaccine candidate strain Re-MuH5-DIVA-ΔNS, has been preserved in China Center for Type Culture Collection, with the preservation number of CCTCC NO: V201741.

An application of the above described vaccine strain in the preparation of avian influenza vaccines.

The applicants have preserved the inventive vaccine strain Re-MuH5-DIVA-ΔNS in China Center for Type Culture Collection, the address of which is Wuhan University, China. The Collection Center received the vaccine strain provided by the applicants on Oct. 19, 2017. The preservation number of the culture issued by the Collection Center is CCTCC NO: V201741, the proposed classification name is H5 avian influenza vaccine candidate strain Re-MuH5-DIVA-ΔNS, the preserved vaccine strain has been identified as viable on Oct. 28, 2017.

The beneficial effects of the invention are:

(1) The application develops a preparation method of a new H5 avian influenza vaccine which differentiates infection from vaccination by introducing NA of influenza B gene as a label.

(2) The present invention has successfully constructed an H5 avian influenza vaccine strain which differentiates infected from vaccinated animals, in which NA gene and HA gene exhibit good compatibility, showing good biological properties in terms of replication and growth, without in vitro passage adaptation, thus avoiding the antigenic variation may be caused by the passage adaptation. Even when passages for the 3rd generation, it still remains low pathogenicity and high titer growth properties in chick-embryos. The present invention has great application values and prominent public health significance.

(3) The highly pathogenic H5 avian influenza not only brings about huge economic losses to the livestock industry, but also seriously threatens public health safety. Conventional H5 avian influenza whole virus inactivated vaccines do have effects, but cannot serologically differentiate antibodies produced from infection from those produced from vaccination, causing a great obstacle in the monitoring and decontamination of avian influenza. The present invention has successfully constructed an H5 avian influenza vaccine strain which differentiates infection from vaccination by using NA of influenza B as a label, having great significance and application values in the prevention, control and decontamination of the H5 avian influenza.

BRIEF DESCRIPTION OF THE DRAWINGS

FIG. 1 is the structure schematic diagram of artificially synthesized A/B chimeric NA gene;

FIG. 2 is the pFLu vector map and the clone schematic diagram of influenza virus gene segments;

FIG. 3 is detecting the reactivity of anti-Re-MuH5-DIVA-ΔNS (A/B chimeric NA) serum with influenza A NA by immunofluorescence.

DESCRIPTION OF THE EMBODIMENTS

The present invention will be illustrated in detail in conjunction with the following specific examples and the accompanying figures, and the embodiments of the invention are not limited to this. For unnoted conventional experimental methods, see "Guideline for Molecular Cloning", the 3rd edition (Sambrook, ed., Science press, 2002).

Example 1 a Preparation Method of Avian Influenza Vaccine Strain Re-MuH5-DIVA-ΔNS Virus (1) Construction of Low Pathogenic HA Mutant Gene The pFlu vector is a kind of bidirectional transcription vector, which may transcribe viral RNA by the human poll promoter, and also transcribe viral mRNA by CMV promoter, thus synthesizing the viral proteins (Hoffmann et al., PNAS, USA 97, 6108-6113, 2000).

With the artificially synthesized wild type H5 gene (A/Duck/Hubei/49/2005), the high conservative sequence (RERRRKRGLF, SEQ ID NO: 8) in the highly pathogenic wild type HA amino acid sequence is mutated into a low pathogenic amino acid sequence (RETRGLF, SEQ ID NO: 9) through site-directed mutagenesis, to obtain the corresponding low pathogenic MuH5HA gene sequence. The modified MuH5HA gene is cloned into the pFlu vector through the BsmBI site to obtain the recombinant plasmid pFlu-MuH5HA, with the construction schematic diagram shown in FIG. 2.

(2) Construction of Low Pathogenic A/B Chimeric NA Gene

Constructing the artificially synthesized A/B chimeric NA gene as shown in FIG. 1, which contains a DNA sequence (SEQ ID NO: 2) for coding an extracellular region amino acid sequence (SEQ ID NO: 1) in influenza B virus NA as the label gene sequence, the sequence containing type B NA extracellular region as shown in SEQ ID NO: 2 deriving from B/Massachusetts/2/2012 in the influenza B virus Yamagata group (Ping J et al, PNAS, 2016, 113(51):E8296-E8305), the label gene sequence further contains packaging signal sequences at its both ends, wherein the 5'-end packaging signal sequence (SEQ ID NO:3) includes the noncoding region sequence, the intracellular region sequence and the transmembrane region sequence, the 3'-end packaging signal sequence is SEQ ID NO:4. The chimeric NA is inserted into the pFlu vector through the BsmBI site to obtain a recombinant plasmid pFlu-PR8-BNA.

(3) Acquisition of Re-MuH5-DIVA-ΔNS Vaccine Strain

For ensuring the safety property of the vaccine strain, the wild type virus NS1 gene is modified, the nucleotide sequence of the modified mutant gene ΔNS is as shown in SEQ ID NO:5. The virus containing the mutant gene ΔNS has lost the function of antagonizing interferons, thus only can grow and propagate in interferon-deficient cells or chick-embryos with underdeveloped interferon systems, therefore having good safety property.

The recombinant vaccine strain Re-MuH5-DIVA-ΔNS is rescued with the classical "6+2" influenza reverse genetic system. Each 0.5 ug of 6 PR8 internal genes pFlu-PR8-PB2, pFlu-PR8-PB1, pFlu-PR8-PA, pFlu-PR8-NP, pFlu-PR8-M, pFlu-PR8-ΔNS and 2 external genes pFlu-MuH5HA, pFlu-PR8-BNA are co-transfected into 293T cells (Lipofectamine 3000). 24 h after transfection, a culture medium containing TPCK-Trypsin at a final concentration of 0.5 ug/ml is exchanged, and 48h after transfection, the cell supernatant is collected, which is inoculated into 8-day-old SPF chick-embryos at 0.2 ml per embryo by allantoic cavity inoculation. After inoculation, chick-embryos are cultured in an incubator at 37° C. for 48 hs. The chick-embryo allantoic fluid (F0 generation) is collected to obtain the vaccine strain Re-MuH5-DIVA-ΔNS, and it is determined whether it has a hemagglutination titer.

The rescued Re-MuH5-DIVA-ΔNS strains become ones with low pathogenicity or without pathogenicity, which only can grow and propagate in interferon-deficient cells or low-age chick-embryos with underdeveloped interferon systems, therefore having good safety property. After incubation on 8-day-old SPF chick-embryos for 48 hours, there is no need for serial passage adaptation on chick-embryos, the HA titers of which may reach 7 log 2. Due to NS1 partial deletion of Re-MuH5-DIVA-ΔNS strain, its growth titer on chick-embryos is lower than that of non-deleted viruses, but better than non-deleted viruses in terms of safety. The obtained virus containing allantoic fluid is inactivated with formalin and further formulated into inactivated vaccines.

The applicants have preserved the inventive vaccine strain Re-MuH5-DIVA-ΔNS in China Center for Type Culture Collection, the address of which is Wuhan University, China. The Collection Center received the vaccine strain provided by the applicants on Oct. 19, 2017. The preservation number of the culture issued by the Collection Center is CCTCC NO: V201741, the proposed classification name is H5 avian influenza vaccine candidate strain Re-MuH5-DIVA-ΔNS, the preserved vaccine strain has been identified as viable on Oct. 28, 2017.

Example 2 a Preparation Method of Avian Influenza Vaccine Strain Re-MuH5-DIVA-ΔNS Virus The preparation method of Example 2 is the same as that of Example 1, except that in constructing the artificially synthesized AB chimeric NA gene as shown in FIG. 1, the DNA sequence for coding the extracellular region protein amino acid sequence in influenza B virus NA is different from that in Example 1, the remaining are all the same as Example 1.

In this Example, the DNA sequence for coding the extracellular region protein amino acid sequence (SEQ ID NO: 6) in influenza B virus NA is shown in SEQ ID NO: 7, which is used as the label gene sequence, the sequence shown in SEQ ID NO: 7 deriving from B/Brisbane/60/2008 of influenza B virus Victoria group (Ping J et al, PNAS, 2016, 113(51):E8296-E8305).

The Re-MuH5-DIVA-ΔNS vaccine strain prepared in the present invention will be further detected for its effects below.

Process: Re-MuH5-DIVA-ΔNS vaccine strains obtained from Examples 1 and 2, PR8-ΔNS (NS-deficient PR8 virus) of the control group 1, PR8-WT (PR8 wild type virus) of the control group 2 are respectively inoculated into 8-day-old chick-embryos at 0.2 ml per embryo for serial passages, the inoculated chick-embryos are cultured in an incubator at 37° C. for 48 hs. The chick-embryo allantoic fluid (F0-generation) is collected for determining its hemagglutinin titer. F0-generation viruses are diluted and inoculated into 10 SPF chick-embryos, cultured for 48hs to obtain viruses which are defined as F1-generation. With the same process, F1-generation viruses are serially passaged to F3-generation.

Results: the detection results aere shown in Table 1. For demonstrating whether type B NA gene of different branches can match with H5 subtype HA (H5-BNA) well, NA genes of representative strains from different groups: B/Brisbane/60/2008 (Victoria group) and Massachusetts/2/2012 (Yamagata group) are selected for study, it is found from the results that type B NA genes of different branches (Victoria group and Yamagata group) both exhibit good matching with H5. Wherein, the titer of Re-MuH5-DIVA-ΔNS vaccine strain of Example 1 possessing Massachusetts/2/2012 (Yamagata group) NA gene on chick-embryo is 7 log 2 HA titer; while the titer of Re-MuH5-DIVA-ΔNS vaccine strain of Example 2 possessing B/Brisbane/60/2008 NA gene on chick-embryos may reach 5.5 log 2 HA titer. Taking F0 and F3 viruses, through amplification of chimeric NA gene by RT-PCR, it is demonstrated by sequencing that chimeric NA gene can be stably passed to progeny viruses.

As also can be seen from Table 1, the growth titers of vaccine strains containing mutant ΔNS are lower than that of wild type by 2 log 2-3 log 2, however, the vaccine strains containing mutant ΔNS are better in terms of safety.

TABLE 1

Growth properties of different chimeric recombinant
H5 avian influenza viruses on chick-embryos

| | HA Titers (log2) | | | |
|---|---|---|---|---|
| Passage Number | Example 1 Re-MuH5-DIVA-ΔNS | Example 2 Re-MuH5-DIVA-ΔNS | Control Group 1 PR8-ΔNS | Control Group 2 PR8-WT |
| F0 | 7 | 5 | 6.5 | 9 |
| F1 | 7 | 5.5 | 7 | 10 |
| F2 | 7.5 | 5 | 7 | 9 |
| F3 | 7 | 5 | 7 | 10 |

For representative influenza B virus strains from different groups: B/Brisbane/60/2008 (Victoria group) and Massachusetts/2/2012 (Yamagata group), the homology between the two NA whole gene nucleotide sequences is 94.9%, the homology of the amino acid sequences is 94.9%; the homology between the two DNA sequences for coding NA protein extracellular region is 95.1%, the homology of the NA protein extracellular region amino acid sequences is 94.6%. Because influenza B is only classified into Victoria group and Yamagata group, it is demonstrated in the invention that representative NA strains from the two groups (Example 1 and Example 2) both have good compatibilities with H5 HA, showing that influenza B virus NA gene may all be used in preparing an H5 avian influenza vaccine strain which differentiates influenza A virus infection from vaccination.

Example 3 Preparation of Re-MuH5-DIVA-ΔNS Inactivated Vaccine 50 ml of F0, F1, F2 or F3-generation allantoic fluids from Re-MuH5-DIVA-ΔNS vaccine strains prepared in the above examples are harvested, and inactivated with a formalin solution at a final concentration of 0.25% at 37° C. for 24 hs. The inactivated allantoic fluids are added into 2% of Tween-80, dissolved sufficiently and then emulsified with white oil containing 3% of Span 80 at a proportion of 1:3, at a shear emulsification rate of 12000 rpm for 3 mins. Upon a dosage form test, a sizing test, a viscosity test, and a stability test, it is determined that the inactivated vaccine is an off-white water-in-oil emulsion with low viscosity, uniform particle sizes, good stability and suitable for injection.

Example 4 Detection of Effects of Re-MuH5-DIVA-ΔNS Inactivated Vaccine on Vaccinating Animals Process: 10 3-week-old SPF chicken are vaccinated with Re-MuH5-DIVA-ΔNS vaccine prepared in the present invention at 0.3 ml per chick by subcutaneous injection at the neck, blood is sampled 21 days after vaccination, serum is isolated and HI antibodies are determined.

Results: it is demonstrated from experiments that Re-MuH5-DIVA-ΔNS stimulates the organism to generate high level of HI antibodies, the average HI titer (log 2) for week 3 is 9.5±0.85. For HA and HI tests, reference to GBT 18936-2003 (diagnosis technology of highly pathogenic avian influenza).

Example 5 Serological Experiments

N1, N2, N6, and N9 genes of the existing influenza A are cloned into pCAGGS eukaryotic expression plasmid through KpnI and NheI sites, which are named as pCAGGS-N1, pCAGGS-N2, pCAGGS-N6, pCAGGS-N9. Each 1 μg of pCAGGS-N1, pCAGGS-N2, pCAGGS-N6, pCAGGS-N9 plasmid is transfected to 293T cells pre-coated on 24-hole cell culture plates. 30 hs after transfection, the reactivities of the following 7 groups of chicken serum with N1, N2, N6, N9 are detected by immunofluorescence.

The profiles of the 7 groups of chicken serum are as below:

Anti-Re-MuH5-DIVA-ΔNS chicken serum: chicken serum which is only vaccinated with the inventive Re-MuH5-DIVA-ΔNS inactivated vaccine;

Anti-H5N1 standard: H5N1 standard serum, purchased from Harbin Veterinary Research Institute.

Anti-H5+H7 serum: clinical serum of vaccinated H5N1 Re-8 strain+H7N9 Re-1 strain whole virus inactivated vaccines.

Anti-N1 chicken serum: one-week-old SPF chicken are vaccinated with 100 μg pCAGGS-N1 (by intramuscular injection) respectively, the whole blood is harvested 4 weeks after vaccination to prepare the serum.

Anti-N2 chicken serum: one-week-old SPF chicken are vaccinated with 100 μg pCAGGS-N2 (by intramuscular injection) respectively, the whole blood is harvested 4 weeks after vaccination to prepare the serum.

Anti-N6 chicken serum: one-week-old SPF chicken are vaccinated with 100 μg pCAGGS-N6 (by intramuscular injection) respectively, the whole blood is harvested 4 weeks after vaccination to prepare the serum.

Anti-N9 chicken serum: one-week-old SPF chicken are vaccinated with 100 μg pCAGGS-N9 (by intramuscular injection) respectively, the whole blood is harvested 4 weeks after vaccination to prepare the serum.

The immunofluorescence process is as below:

1) Into each cell is added 0.5 ml of 4% paraformaldehyde for immobilization for 20 minutes, and then washed with PBS for three times.

2) It is permeated with 0.2% Triton X 100 for 10 minutes, and then washed with PBS for three times.

3) It is blocked with 5% BSA for 1 hour, and then washed with PBS for three times.

4) Primary antibodies are diluted with PBS containing 1% BSA by corresponding factors (anti-Re-MuH5-DIVA-ΔNS, anti-H5N1 standard, anti-H5+H7, for 100-fold; anti-N1/N2/N6/N9, for 20-fold), and added into each hole at 0.5 ml, incubated in a wet box at 37° C. for 1 hour, and then washed with PBS for three times.

5) Anti-Chicken secondary antibodies (Alexa Fluor 594 Donkey Anti-Chicken IgY) are diluted with PBS containing 1% BSA for 200-fold, added into each hole at 0.5 ml, incubated at room temperature for 0.5 hours, and then washed with PBS for three times.

6) Observing with a fluorescence microscope.

Results: Influenza N1, N2, N6 and N9 neuraminidases are respectively expressed in 293T cells, the immunofluorescence process is used to detect whether serum has reacted with N1, N2, N6 and N9 3 weeks after vaccination with Re-MuH5-DIVA-ΔNS. It is found that the anti-Re-MuH5-DIVA-ΔNS serum does not cross react with N1, N2, N6 and N9 proteins (e.g., as shown in Table 2 and FIG. 3), both clinical serum vaccinated with the existing whole type A virus vaccines (H5N1 Re-8 strain+H7N9 Re-1 strain) and anti-H5N1 standard serum can strongly react with N1 protein. It is demonstrated from this experiment that vaccination with the Re-MuH5-DIVA-ΔNS vaccine can not only induce high level of HI antibodies, but also can differentiate infected from vaccinated animals, which overcomes the disadvantage that the existing H5 subtype whole virus vaccine is unable to differentiate infected from vaccinated animals.

TABLE 2

Comparison of reactivities between chicken sera vaccinated with different antigens and various NA subtypes

| Antibodies | | Antigens | | | |
|---|---|---|---|---|---|
| | | N1 | N2 | N6 | N9 |
| Anti-Re-MuH5-DIVA-ANS | HI: 9log2 | No reactivity | No reactivity | No reactivity | No reactivity |
| Anti-H5N1 standard | HI: 8log2 | Reactivity | ND | ND | ND |
| Anti-H5 + H7 | HI: 8log2 (H5) | Reactivity | ND | ND | ND |
| Anti-N1 | HI: N/A | Reactivity | ND | ND | ND |
| Anti-N2 | HI: N/A | ND | Reactivity | ND | ND |
| Anti-N6 | HI: N/A | ND | ND | Reactivity | ND |
| Anti-N9 | HI: N/A | ND | ND | ND | Reactivity |

Example 6 a Preparation Method of an H5 Avian Influenza Vaccine Strain Re-MuH5-DIVA-ΔNS which Differentiates Influenza a Virus Infection from Vaccination The preparation method of Example 6 is the same as that of Example 1, except that in constructing the artificially synthesized AB chimeric NA gene as shown in FIG. 1, the influenza B virus NA sequence used is the DNA sequence for coding NA whole protein sequence, the remaining are all the same as Example 1, wherein, the DNA sequence of NA derived from the NA whole gene sequence of B/Massachusetts/2/2012 in the Yamagata group of influenza B virus (Ping J et al, PNAS, 2016, 113(51): E8296-E8305).

The above examples are the preferable embodiments of the invention, however, the detailed description of the invention is not limited to the examples described above, any other changes, modifications, substitutions, combinations, simplifications made without deviating from the spirit and principle of the invention should all be considered as equivalent replacements, which are all within the scope of the present invention.

What is claimed is:

1. An H5 avian influenza vaccine strain, comprising a label gene sequence and an H5 subtype HA gene or a mutated H5 subtype HA gene, wherein the label gene sequence comprising a DNA sequence coding an influenza B virus NA protein extracellular region amino acid sequence set forth in SEQ ID NO: 1 or SEQ ID NO: 6, or comprising a DNA sequence coding an amino acid sequence having at least 90% homology, at least 92% homology, at least 95% homology, or at least 98% homology with the extracellular region amino acid sequence set forth in SEQ ID NO: 1 or SEQ ID NO: 6;

alternatively, the label gene sequence comprising a DNA sequence set forth in SEQ ID NO: 2 or SEQ ID NO: 7 coding the extracellular region amino acid sequence in influenza B virus NA gene, or comprising a sequence having at least 90% homology, at least 92% homology, at least 95% homology, or at least 98% homology with the DNA sequence set forth in SEQ ID NO: 2 or SEQ ID NO: 7;

and wherein the mutated H5 subtype HA gene has been mutated to encode RETRGLF (SEQ ID NO: 9) in place of RERRRKRGLF (SEQ ID NO: 8).

2. The vaccine strain of claim 1, wherein the influenza B virus comprises influenza B viruses of Victoria group and Yamagata group.

3. The vaccine strain of claim 2, wherein the influenza B virus comprises virus strains B/Massachusetts/2/2012, B/Brisbane/60/2008, B/Yamagata/16/1988, or B/Malaysia/2506/04.

4. The vaccine strain of claim 1, wherein the label gene sequence further comprises a packaging signal sequence at both ends, wherein the packaging signal is a packaging signal of H1 subtype NA set forth in SEQ ID NO: 3 or SEQ ID NO: 4, or a packaging signal sequence having at least 80% homology, at least 85% homology, at least 90% homology, or at least 95% homology with the packaging signal of H1 subtype NA.

5. The vaccine strain of claim 1, wherein the label gene sequence further comprises packaging signal sequences at both ends, wherein the 5'-end packaging signal sequence comprises a noncoding region sequence, an intracellular region sequence, and a transmembrane region sequence.

6. The vaccine strain of claim 5, wherein the intracellular region sequence encodes 5~7 amino acids.

7. The vaccine strain of claim 5, wherein the transmembrane region sequence encodes 24~32 amino acids.

8. The vaccine strain of claim 5, wherein the 5'-end packaging signal sequence of the label gene sequence comprises SEQ ID NO:3, or a sequence having at least 80% homology, at least 85% homology, at least 90% homology, or at least 95% homology with SEQ ID NO:3.

9. The vaccine strain of claim 1, wherein the label gene sequence further comprises packaging signal sequences at both ends, wherein the 3'-end packaging signal sequence comprises SEQ ID NO:4, or a sequence having at least 80% homology, at least 85% homology, at least 90% homology, or at least 95% homology with SEQ ID NO:4.

10. A preparation method of an H5 avian influenza vaccine strain, comprising:

contacting a label gene sequence with an HA gene or a mutated H5 subtype HA gene of H5 avian influenza virus over a reverse genetic system; and obtaining a recombinant H5 avian influenza vaccine strain;

wherein:

the mutated H5 subtype HA gene has been mutated to encode RETRGLF (SEQ ID NO: 9) In place of RERRRKRGLF (SEQ ID NO: 8);

the label gene sequence comprising a DNA sequence for coding an influenza B virus NA protein extracellular region amino acid sequence set forth in SEQ ID NO: 1 or SEQ ID NO: 6, or comprising a DNA sequence for coding an amino acid sequence comprising at least 90% homology, at least 92% homology, at least 95% homology, or at least 98% homology with the extracellular region amino acid sequence set forth in SEQ ID NO: 1 or SEQ ID NO: 6;

alternatively, the label gene sequence comprising a DNA sequence set forth in SEQ ID NO: 2 or SEQ ID NO: 7 for coding an extracellular region amino acid sequence in influenza B virus NA gene, or comprising a sequence comprising at least 90% homology, at least 92% homology, at least 95% homology, or at least 98% homology with the DNA sequence set forth in SEQ ID NO: 2 or SEQ ID NO: 7.

11. The method of claim 10, wherein the label gene sequence further comprises packaging signal sequences at both ends.

12. The method of claim 11, wherein the 5'-end packaging signal sequence of the label gene sequence comprises SEQ ID NO:3, or a sequence having at least 80% homology, at least 85% homology, at least 90% homology, or at least 95% homology with SEQ ID NO:3.

13. The method of claim 11, wherein the 3'-end packaging signal sequence of the label gene sequence comprises SEQ ID NO:4, or a sequence having at least 80% homology, at least 85% homology, at least 90% homology, or at least 95% homology with SEQ ID NO:4.

14. The method of claim 10, further comprising 6 additional PR8 internal genes, wherein the 6 additional PR8 internal genes comprise a wild type NS, a mutated ΔNS gene, PB2, PB1, PA, NP, or M; wherein ΔNS is a mutated NS gene, and the nucleotide sequence of ΔNS is as set forth in SEQ ID NO:5.

15. An H5 avian influenza vaccine strain, which is named as H5 avian influenza vaccine candidate strain Re-MuH5-DIVA-ΔNS, has been preserved in China Center for Type Culture Collection, with the preservation number of CCTCC NO: V201741.

16. An avian influenza vaccine, comprising the vaccine strain of claim 15.

* * * * *

SEQUENCE LISTING

<160> NUMBER OF SEQ ID NOS: 9

<210> SEQ ID NO 1
<211> LENGTH: 407
<212> TYPE: PRT
<213> ORGANISM: Artificial Sequence
<220> FEATURE:
<223> OTHER INFORMATION: an extracellular region amino acid sequence

<400> SEQUENCE: 1

```
Val Gln Ala Val Asn His Ser Ala Ala Lys Gly Val Thr Leu Leu Leu
1               5                   10                  15

Pro Glu Pro Glu Trp Thr Tyr Pro Arg Leu Ser Cys Pro Gly Ser Thr
            20                  25                  30

Phe Gln Lys Ala Leu Leu Ile Ser Pro His Arg Phe Gly Glu Ile Lys
        35                  40                  45

Gly Asn Ser Ala Pro Leu Ile Ile Arg Glu Pro Phe Ile Ala Cys Gly
    50                  55                  60

Pro Thr Glu Cys Lys His Phe Ala Leu Thr His Tyr Ala Ala Gln Pro
65                  70                  75                  80

Gly Gly Tyr Tyr Asn Gly Thr Arg Glu Asp Arg Asn Lys Leu Arg His
                85                  90                  95

Leu Ile Ser Val Lys Leu Gly Lys Ile Pro Thr Val Glu Asn Ser Ile
            100                 105                 110

Phe His Met Ala Ala Trp Ser Gly Ser Ala Cys His Asp Gly Lys Glu
        115                 120                 125

Trp Thr Tyr Ile Gly Val Asp Gly Pro Asp Ser Asn Ala Leu Leu Lys
    130                 135                 140

Ile Lys Tyr Gly Glu Ala Tyr Thr Asp Thr Tyr His Ser Tyr Ala Lys
145                 150                 155                 160

Asn Ile Leu Arg Thr Gln Glu Ser Ala Cys Asn Cys Ile Gly Gly Asp
                165                 170                 175

Cys Tyr Leu Met Ile Thr Asp Gly Pro Ala Ser Gly Val Ser Glu Cys
            180                 185                 190

Arg Phe Leu Lys Ile Arg Glu Gly Arg Ile Ile Lys Glu Ile Phe Pro
```

```
                    195                 200                 205
Thr Gly Arg Val Lys His Thr Glu Glu Cys Thr Cys Gly Phe Ala Ser
            210                 215                 220

Asn Lys Thr Ile Glu Cys Ala Cys Arg Asp Asn Arg Tyr Thr Ala Lys
225                 230                 235                 240

Arg Pro Phe Val Lys Leu Asn Val Glu Thr Asp Thr Ala Glu Ile Arg
                245                 250                 255

Leu Met Cys Thr Glu Thr Tyr Leu Asp Thr Pro Arg Pro Asn Asp Gly
                260                 265                 270

Ser Ile Thr Gly Pro Cys Glu Ser Asp Gly Asp Lys Gly Ser Gly Gly
                275                 280                 285

Ile Lys Gly Gly Phe Val His Gln Arg Met Ala Ser Lys Ile Gly Arg
            290                 295                 300

Trp Tyr Ser Arg Thr Met Ser Lys Thr Lys Arg Met Gly Met Gly Leu
305                 310                 315                 320

Tyr Val Lys Tyr Asp Gly Asp Pro Trp Thr Asp Ser Glu Ala Leu Ala
                325                 330                 335

Leu Ser Gly Val Met Val Ser Met Glu Glu Pro Gly Trp Tyr Ser Phe
                340                 345                 350

Gly Phe Glu Ile Lys Asp Lys Lys Cys Asp Val Pro Cys Ile Gly Ile
                355                 360                 365

Glu Met Val His Asp Gly Gly Lys Thr Thr Trp His Ser Ala Ala Thr
            370                 375                 380

Ala Ile Tyr Cys Leu Met Gly Ser Gly Gln Leu Leu Trp Asp Thr Val
385                 390                 395                 400

Thr Gly Val Asp Met Ala Leu
                405

<210> SEQ ID NO 2
<211> LENGTH: 1224
<212> TYPE: DNA
<213> ORGANISM: Artificial Sequence
<220> FEATURE:
<223> OTHER INFORMATION: the sequence containing type B NA extracellular
      region

<400> SEQUENCE: 2
gttcaggctg taaatcattc tgcagcaaaa ggggtgacac ttcttctccc agaaccggaa      60
tggacatacc ctcgttttat cttgcccggc tcaacctttc agaaagcact cctaattagc     120
ccccatagat tcggagaaat caaaggaaac tcagctccct tgataataag gaaccttttt     180
attgcttgtg gaccaacgga atgcaaacac tttgctctaa cccattatgc agctcaacca     240
gggggatact acaatggaac aagagaagac agaaacaagc tgaggcatct aatttcagtc     300
aaattgggca aaatcccaac agtagaaaac tccattttcc acatggcagc ttggagcggg     360
tccgcatgcc atgatggtaa agaatggaca tatatcggag ttgatggccc cgacagtaat     420
gcattgctca aaataaaata tggagaagca tatactgaca cataccattc ctatgcaaaa     480
aacatcctaa ggacacaaga agtgcctgcc aattgcatcg ggggagattg ttatcttatg     540
ataactgatg gccagcttc aggggttagt gaatgcagat tcttaagat tcgagagggc     600 agaataataa agaaatatt tccaacagga agtaaaac atactgagga atgcacatgc     660
ggatttgcca gcaacaaaac catagaatgt gcttgtagag ataaccgtta cacagcaaaa     720 agacccttg tcaaattaaa tgtggagact gatacagcgg aaataagatt gatgtgcaca     780
gagacttatt tggacacccc cagaccaaat gatggaagca taacagggcc ttgcgaatct     840
```

```
gatggggaca aagggagtgg aggcatcaag ggaggatttg ttcatcaaag aatggcatcc      900
aagattggaa ggtggtactc tcgaacgatg tctaaaacca aaagaatggg gatgggactg      960
tatgtaaaat atgatggaga cccatggact gacagtgaag cccttgctct tagtggagta     1020
atggtttcaa tggaagaacc tggttggtat tcctttggct tcgaaataaa agataagaaa     1080
tgtgatgtcc cctgtattgg gatagaaatg gtacatgatg gtgggaaaac gacttggcac     1140
tcagcagcaa cagccattta ttgtttaatg ggctcaggac aattgctgtg ggacactgtc     1200
acaggtgttg atatggctct gtaa                                            1224

<210> SEQ ID NO 3
<211> LENGTH: 203
<212> TYPE: DNA
<213> ORGANISM: Artificial Sequence
<220> FEATURE:
<223> OTHER INFORMATION: 5'-end packaging signal sequence

<400> SEQUENCE: 3
agcaaaagca ggggtttaaa atgaatccaa atcagaaaat aataaccatt ggatcaatct       60
gtctggtagt cggactaatt agcctaatat tgcaaatagg gaatataatc tcaatatgga      120
ttagccattc aattcaaact ggaagtcaaa accatactgg aatatgcaac caaaacatca      180
ttacctataa aaatagcacc tgg                                              203

<210> SEQ ID NO 4
<211> LENGTH: 185
<212> TYPE: DNA
<213> ORGANISM: Artificial Sequence
<220> FEATURE:
<223> OTHER INFORMATION: 3'-end packaging signal sequence

<400> SEQUENCE: 4
gaggccgtgc ttctggggttg aattaatcag gggacgacct aaagaaaaaa caatctggac       60
tagtgcgagc agcatttctt tttgtggcgt gaatagtgat actgtagatt ggtcttggcc      120
agacggtgct gagttgccat tcagcattga caagtagtct gttcaaaaaa ctccttgttt      180
ctact                                                                  185

<210> SEQ ID NO 5
<211> LENGTH: 890
<212> TYPE: DNA
<213> ORGANISM: Artificial Sequence
<220> FEATURE:
<223> OTHER INFORMATION: the nucleotide sequence of DeltaNS

<400> SEQUENCE: 5
agcaaaagca gggtgacaaa aacataatgg atccaaacac tgtgtcaagc tttcaggtag       60
attgctttct ttggcatgtc cgcaaacgag ttgcagacca agaactaggc gatgccccat      120
tccttgatcg gcttcgccga gatcagaaat ccctaagagg aagggcagt actctcggtc      180 tggacatcaa gacagccaca cgtgctggaa agcagatagt ggagcggatt ctgaaagaag      240
aatccgatga ggcacttaaa atgaccatgg cctctgtacc tgcgtcgcgt tacctaactg      300
acatgactct tgaggaaatg tcatgataat ggtccatgct catacccaag cagaaagtgg      360
caggccctct ttgtatcaga atggaccagg cgatcatgga taagaacatc atactgaaag      420
cgaacttcag tgtgattttt gaccggctgg agactctaat attgctaagg gctttcaccg      480
aagagggagc aattgttggc gaaatttcac cattgccttc tcttccagga catactgctg      540
```

-continued

```
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga agataacaga gaatagtttt    780
gagcaaataa catttatgca agccttacat ctattgcttg aagtggagca agagataaga    840
actttctcgt ttcagcttat ttagtactaa aaaacaccct tgtttctact               890
```

<210> SEQ ID NO 6
<211> LENGTH: 407
<212> TYPE: PRT
<213> ORGANISM: Artificial Sequence
<220> FEATURE:
<223> OTHER INFORMATION: the extracellular region protein amino acid
      sequence

<400> SEQUENCE: 6

Val Gln Ala Val Asn Arg Ser Ala Thr Lys Gly Val Thr Leu Leu Leu
1               5                   10                  15

Pro Glu Pro Glu Trp Thr Tyr Pro Arg Leu Ser Cys Pro Gly Ser Thr
                20                  25                  30

Phe Gln Lys Ala Leu Leu Ile Ser Pro His Arg Phe Gly Glu Thr Lys
            35                  40                  45

Gly Asn Ser Ala Pro Leu Ile Ile Arg Glu Pro Phe Ile Ala Cys Gly
        50                  55                  60

Pro Asn Glu Cys Lys His Phe Ala Leu Thr His Tyr Ala Ala Gln Pro
65                  70                  75                  80

Gly Gly Tyr Tyr Asn Gly Thr Arg Gly Asp Arg Asn Lys Leu Arg His
                85                  90                  95

Leu Ile Ser Val Lys Leu Gly Lys Ile Pro Thr Val Glu Asn Ser Ile
            100                 105                 110

Phe His Met Ala Ala Trp Ser Gly Ser Ala Cys His Asp Gly Lys Glu
        115                 120                 125

Trp Thr Tyr Ile Gly Val Asp Gly Pro Asp Asn Asn Ala Leu Leu Lys
    130                 135                 140

Val Lys Tyr Gly Glu Ala Tyr Thr Asp Thr Tyr His Ser Tyr Ala Asn
145                 150                 155                 160

Lys Ile Leu Arg Thr Gln Glu Ser Ala Cys Asn Cys Ile Gly Gly Asn
                165                 170                 175

Cys Tyr Leu Met Ile Thr Asp Gly Ser Ala Ser Gly Val Ser Glu Cys
            180                 185                 190

Arg Phe Leu Lys Ile Arg Glu Gly Arg Ile Ile Lys Glu Ile Phe Pro
        195                 200                 205

Thr Gly Arg Val Lys His Thr Glu Glu Cys Thr Cys Gly Phe Ala Ser
    210                 215                 220

Asn Lys Thr Ile Glu Cys Ala Cys Arg Asp Asn Ser Tyr Thr Ala Lys
225                 230                 235                 240

Arg Pro Phe Val Lys Leu Asn Val Glu Thr Asp Thr Ala Glu Ile Arg
                245                 250                 255

Leu Met Cys Thr Asp Thr Tyr Leu Asp Thr Pro Arg Pro Asn Asp Gly
            260                 265                 270

Ser Ile Thr Gly Pro Cys Glu Ser Asn Gly Asp Lys Gly Ser Gly Gly
        275                 280                 285

Ile Lys Gly Gly Phe Val His Gln Arg Met Glu Ser Lys Ile Gly Arg
    290                 295                 300

Trp Tyr Ser Arg Thr Met Ser Lys Thr Glu Arg Met Gly Met Gly Leu
305                 310                 315                 320

Tyr Val Lys Tyr Asp Gly Asp Pro Trp Ala Asp Ser Asp Ala Leu Ala
            325                 330                 335

Phe Ser Gly Val Met Val Ser Met Lys Glu Pro Gly Trp Tyr Ser Phe
        340                 345                 350

Gly Phe Glu Ile Lys Asp Lys Lys Cys Asp Val Pro Cys Ile Gly Ile
    355                 360                 365

Glu Met Val His Asp Gly Lys Glu Thr Trp His Ser Ala Ala Thr
370                 375                 380

Ala Ile Tyr Cys Leu Met Gly Ser Gly Gln Leu Leu Trp Asp Thr Val
385                 390                 395                 400

Thr Gly Val Asp Met Ala Leu
            405

<210> SEQ ID NO 7
<211> LENGTH: 1224
<212> TYPE: DNA
<213> ORGANISM: Artificial Sequence
<220> FEATURE:
<223> OTHER INFORMATION: the DNA sequence for coding the extracellular
      region protein amino acid sequence

<400> SEQUENCE: 7
gttcaggctg tgaaccgttc tgcaacaaaa ggggtgacac ttcttctccc agaaccggag      60
tggacatacc cgcgtttatc ttgcccgggc tcaacctttc agaaagcact cctaattagc     120
cctcatagat tcggagaaac caaggaaac tcagctccct tgataataag gaacctttt      180 attgcttgtg gaccaaatga atgcaaacac tttgctctaa cccattatgc agcccaacca     240
gggggatact acaatggaac aagaggagac agaaacaagc tgaggcatct aatttcagtc     300
aaattgggca aaatcccaac agtagaaaac tccattttcc acatggcagc atggagcggg     360
tccgcgtgcc atgatggtaa ggaatggaca tatatcggag ttgatggccc tgacaataat     420
gcattgctca agtaaaaata tggagaagca tatactgaca cataccattc ctatgcaaac     480
aaaatcctaa gaacacaaga agtgcctgc aattgcatcg ggggaaattg ttatcttatg     540
ataactgatg gctcagcttc aggtgttagt gaatgcagat tcttaagat tcgagagggc     600 cgaataataa aagaaatatt tccaacagga agagtaaaac acactgagga atgcacatgc     660
ggatttgcca gcaataaaac catagaatgt gcctgtagag ataacagtta cacagcaaaa     720
agaccttttg tcaaattaaa cgtggagact gatacagcag aaataagatt gatgtgcaca     780
gatacttatt tggacacccc cagaccaaac gatggaagca taacaggccc ttgtgaatct     840
aatgggacga aagggagtgg aggcatcaag ggaggatttg ttcatcaaag aatgaatcc     900 aagattggaa ggtggtactc tcgaacgatg tctaaaactg aaaggatggg gatgggactg     960
tatgtcaagt atgatggaga cccatgggct gacagtgatg ccctagcttt tagtggagta    1020 atggttcaa tgaaagaacc tggttggtac tcctttggct cgaaataaa agataagaaa    1080 tgcgatgtcc cctgtattgg gatagagatg gtacatgatg gtggaaaaga gacttggcac    1140
tcagcagcaa cagccattta ctgtttaatg ggctcaggac agctgctgtg ggacactgtc    1200
acaggtgttg acatggctct gtaa                                           1224

<210> SEQ ID NO 8
<211> LENGTH: 10
<212> TYPE: PRT

```
<213> ORGANISM: Artificial Sequence
<220> FEATURE:
<223> OTHER INFORMATION: Amino acid sequence in wild type HA protein

<400> SEQUENCE: 8

Arg Glu Arg Arg Arg Lys Arg Gly Leu Phe
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Mutant amino acid sequence in HA protein

<400> SEQUENCE: 9

Arg Glu Thr Arg Gly Leu Phe
1               5
```